United States Patent [19]

Heiliger et al.

[11] Patent Number: 5,409,964
[45] Date of Patent: Apr. 25, 1995

[54] PHOTOCHEMICALLY LINKABLE POLYMERS

[75] Inventors: Ludger Heiliger; Eberhard Kuckert, both of Leverkusen, Germany

[73] Assignee: Bayer Aktiengesellschaft, Leverkusen, Germany

[21] Appl. No.: 946,566

[22] Filed: Sep. 18, 1992

[30] Foreign Application Priority Data

Sep. 30, 1991 [DE] Germany ............... 41 32 466.8

[51] Int. Cl.⁶ .................. C08F 2/46; C08F 8/30; C08F 20/08; C08F 20/56
[52] U.S. Cl. .................... 522/50; 522/63; 525/54.1; 525/54.11; 525/123; 525/327.4; 525/329.3; 525/329.4; 525/329.5; 525/330.3; 525/330.7; 525/333.3
[58] Field of Search .............. 522/50, 63; 525/54.1, 525/54.11, 123, 329.4, 329.3, 329.7, 330.3, 330.7, 333.3, 329.5

[56] References Cited

U.S. PATENT DOCUMENTS 4,387,154  6/1983  Whitmore ..................... 430/116
4,404,289  9/1983  Masuda et al. ................ 436/544
4,473,652  9/1984  Okazaki et al. ............... 436/541
5,045,433  9/1991  Kakumaru et al. .............. 522/63
5,089,377  2/1992  Kakumaru et al. ............. 430/281

FOREIGN PATENT DOCUMENTS 0187332    7/1986  European Pat. Off. .
WO89/05329 6/1989  WIPO .

*Primary Examiner*—John Kight, III
*Assistant Examiner*—P. Hampton-Hightower
*Attorney, Agent, or Firm*—Connolly and Hutz

[57] ABSTRACT

Photochemically linkable polymers corresponding to formula (I)

$$P\text{-}(A)_n \qquad (I)$$

in which
  P is a polymer component,
  A is a photochemically reactive unit and
  n is the number 1 or 2, and their use for immunological purposes.

11 Claims, No Drawings

PHOTOCHEMICALLY LINKABLE POLYMERS

This invention relates to new photochemically linkable polymers, to a process for their production and to their use for the photochemical immobilization and/or marking of biologically active molecules, such as for example proteins or nucleic acids.

In WO 89/053 29, polymer surfaces of preformed, basically water-insoluble polymers, such as microtitration plates of polystyrene or polymethyl methacrylate, are modified with photochemically active, biotinylated compounds in aqueous solution by a polymer-analogous photoreaction. The photochemical linking of the photochemically reactive monomeric compound to the polymer takes place in heterogeneous reaction with only the wetted pan of the polymer plates, i.e. only on the contacting surfaces of the two phases. In addition, the high surface tension of the water which is reflected in the poor wettability of the plastic plate, provides for extremely poor contact between the two components to be reacted. This results in a quamum yield of the photolinking reaction and in a long irradiation time (1.5 h) if linking reactions are to be successfully carried out at all. In principle, the polymer surface thus modified can only be reached for the immobilization of biomolecules through the multistage linking known per se of titration plates-biotin-avidin-(or streptavidin-) biotin-biomolecule sequence. To this end, the biomolecule to be immobilized first has to be functionalized with biotin to enable subsequent immobilization. The actual immobilization of a biotinylated biomolecule is only experimentally accessible in an extremely narrow concentration range of the photochemical linking reagent because (strept)avidin—as a polyfunctional reagent for biotin—can react equally as a bridging member in the linking sequence and as a blocking agent (i.e. crosslinking between the individual polymer molecules of the titration plates). This means that, for low concentrations of biotin anchor groups, linking to (biotinylated) biomolecules via (strept-)avidin is only possible in low yields whereas, for high concentrations of biotin anchor groups, total crosslinking with the microtitration plates takes place, so that there is no further linking with (biotinylated) biomolecules.

By contrast, polymers according to the invention can be directly photochemically linked in homogeneous phase to native biomolecules, such as nucleic acids or proteins, in a single reaction step without modification or functionalization and may therefore be used not only for direct, specific immobilization, but also for the quantification of biomolecules through photochemical marking. By virtue of the selective incorporation of the photochemically reactive component, no crosslinking occurs, even at high conversions of the linking reaction.

The present invention relates to photochemically linkable polymers corresponding to general formula (I)

$$P\text{-}(A)_n \quad (I)$$

in which
P is a polymer component,
A is a photochemically reactive unit and
n is the number 1 or 2.

The polymeric component P may be linear, branched or crosslinked and may be prepared, for example, by radical polymerization or polycondensation. Polyurethanes and polyureas are also suitable.

Suitable monomer units for the polymeric component are, for example, acrylic, methacrylic, vinyl or styryl units or mixtures thereof, for example in the form of their acid, ester, amide or ketone derivatives. The monomer units may contain reactive or activatable groups which allow covalent bonding, for example to a chelating agent. Groups such as these may be, for example, acid halide, imide ester, benztriazolyl, isocyanato, isothiocyanate, oxirane or diimide groups. Preferred monomer units are (meth)acrylic acid chloride, (meth)acrylic acid N-hydroxysuccinimidoester, (meth)acrylic acid N-hydroxyphthalimidoester, N-(meth)acryloyl benztriazole, 3- or 4-isothiocyanatophenyl(meth)acrylate, 2-isocyanatoethyl(meth)acrylate, isocyanatoisopropenyl benzene, isopropenyl-α,α-dimethylbenzyl isocyanate, vinyl oxirane or a combination of (meth)acrylic acid with carbodiimides.

In the context of the invention, chelating agents are understood to be any structures which are capable of reversibly complexing monovalent, divalent and trivalent metal ions.

Possible chelating agents are, for example, those obtainable by the use of

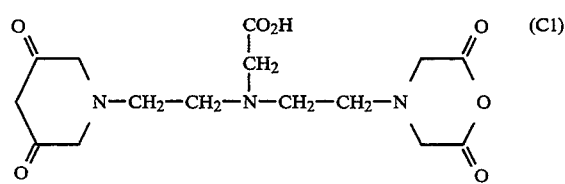

(in some cases after opening of cyclic anhydride functions) and compounds corresponding to the following formulae

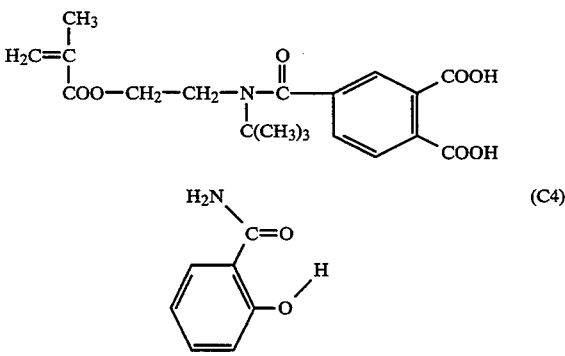

salicyclic acid amide

Several suitable chelating agents are described, for example, in L. Yuanfang and W. Chuanchu, Pure and Applied Chemistry, Vol. 63, No. 3, 427–463 (1991).

Compound C3 is obtained by reaction of benzene tricarboxylic anhydride chloride with n-tert.butyl-2-aminoethyl methacrylate in an organic solvent, such as dioxane for example, at temperatures of −30° to 110° C., optionally in the presence of a base, such as for example triethyl amine or pyridine, and subsequent saponification of the anhydride function.

Suitable monomer units are compounds corresponding to formula (II)

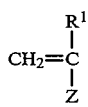

in which

Z is hydrogen, $C_{1-20}$ alkyl, preferably $C_{1-15}$ alkyl and, more preferably, $C_{1-6}$ alkyl, —CO—OR$^2$, —CO—NR$^3$R$^4$ or —OCR$^5$ and $R^1$, $R^2$, $R^3$, $R^4$ and $R^5$ independently of one another represent hydrogen or $C_{1-20}$ alkyl, preferably $C_{1-15}$ alkyl and, more preferably, $C_{1-6}$ alkyl. Other suitable monomer units are, for example, styrene, α-methyl styrene or compounds corresponding to formula (III)

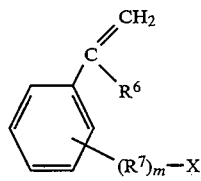

in which $R^6$ is hydrogen or methyl, $R^7$ is $CH_2$ or $SO_2$, m is 0 or 1 and X is halogen, $SO_2$—$CH_2$—$CH_2$ halogen, OMe, SO—$CH_3$ or methyl.

Halogen is preferably chlorine, bromine or iodine, more preferably chlorine or bromine and Me is an equivalent of a metal, for example, sodium, potassium, cesium or ammonium.

Other suitable monomer units are 1- and 2-vinyl naphthalene, 1-vinyl carbazole and compounds which are analogous to those corresponding to formula (III), but contain naphthalene or carbazole as their aromatic base and also (meth)acrylamides and (meth)acrylates derived from aromatic amines, phenols, aromatic hydroxycarboxylic, hydroxysulfonic, aminocarboxylic and aminosulfonic acids and corresponding to formula (IV)

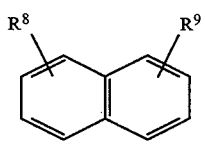

in which $R^8$ is hydrogen, $SO_3H$, COOH, $SO_3Me$ or COOMe, where Me is an equivalent of a metal, such as sodium for example, and $R^9$ represents

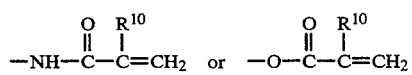

where $R^{10}$ is hydrogen or methyl.

The polycondensates, polyurethanes or polyureas are known and general methods for their production are described in Houben-Weyl, Makromolekulare Chemie, Part 1, (1987), pages 555–608. In addition, several of these polymers are described in detail for various applications in Part 2, pages 1443–1457 and 1561–1751.

The monomer units of component P may contain water-solubilizing ionic or nonionic groups. The monomers preferably contain ionic water-solubilizing groups.

The monomer units in question may be, for example, acrylic acid, methacrylic acid acrylamide, methacrylamide or derivatives thereof, for example 2-acryloylamino-2-methyl propanesulfonic acid, dialkylaminoalkyl(meth)acrylates and dialkylaminoalkyl(meth)acrylamides, such as dimethylaminoethyl methacrylate, dimethylaminopropyl acrylamide and the quaternized compounds derived from these (meth)acrylates and (meth)acrylamides. Also suitable are, for example, N-vinyl pyrrolidone, N-vinyl piperidone, N-vinyl caprolactam, N-vinyl formamide, N-vinyl acetamide, N-vinyl-N-methyl acetamide and N-vinyl-O-methyl urethane.

The monomer units mentioned above may be combined with one another in the form of statistical, alternating or branched block, graft or comb polymers. Statistical copolymers and homopolymers are preferred.

Preferred monomer units contain water-solubilizing groups to make the polymer soluble in water which is of advantage for photolinking with biologically active substrates. Among the water-solubilizing groups, carboxylic and sulfonic acid groups and conjugated bases thereof are particularly preferred. Polymeric components P, which have a chelating effect for monovalent, divalent and trivalent cations, such as for example lanthanides, more particularly europium, are particularly preferred.

Uncrosslinked, nonionic polymers P have average molecular weights ($\overline{M}_w$) in the range from 1,000 to 10,000,000 and preferably in the range from 5,000 to 2,000,000. Polycondensation products preferably have average molecular weights of 5,000 to 100,000.

Ionic polymers generally have a limiting viscosity of at least 0.1 dl/g, preferably 0.5 to 20 dl/g and, more preferably, 1 to 10 dl/g, as measured on a 0.9% aqueous NaCl solution at 20° C.

Suitable photochemically active units A are, for example, acridine dyes, furocoumarins, phenanthridines, phenazines, phenothiazines, quinolines, anthracyclines, netropsin, distamycin or bis-benzimidazoles, cf. the following list (Table 1).

TABLE 1

| List of photochemically active units A | |
|---|---|
| Unit A | Literature |
| Acridine dyes: | Lerman, J. Mol. Biol. 3:18 (1961); Bloomfield et al., "Physical Chemistry of Nucleic acids", Chapter 7, pp. 429–476, Harper and Rowe, N.Y. (1974) |
| proflavine, acridine orange, quinacridine, acriflavine | Miller et al., Biopolymers 19:2091 (1980) |
| Phenanthridines: | Bloomfield et al., loc. cit. Miller et al., loc. cit. |
| ethidium, coraline | Wilson et al., J.Med.Chem. 19:1261 (1976) |
| ellipticin, ellipticin cation and derivatives | Fety et al. FEBS Letters 17:321 (1971); Kohn et al., Cancer Res. 35:71 (1976); Le Pecq et al., PNAS (USA) 71:5078 (1974); Pelaprat et al., J. Med. Chem. 23:1330 (1980) |

TABLE 1-continued

List of photochemically active units A

| Unit A | Literature |
|---|---|
| Phenazines:<br>5-methyl phenazine cation | Bloomfield et al., loc. cit. |
| Phenothiazines:<br>chlorpromazine | Bloomfield et al., loc. cit. |
| Quinolines:<br>chloroquinone, quinine | Bloomfield et al., loc. cit. |
| Anthracyclines:<br>B-Rhodomycin A<br>Daunamycin | Bloomfield et al., loc. cit. |
| Furocoumarins: | |
| angelicin | Venema et al., MGG, Mol. Gen. Genet. 179;1 (1980) |
| 4,5'-dimethyl angelicin | Vedaldi et al., Chem. Biol. Interact 36: 275 (1981) |
| psoralene | Marciani et al., Z. Naturforsch. B 27 (2): 196 (1972) |
| 8-methoxypsoralene | Belognzov et al., Mutat. Res. 84:11 (1981); Scott et al., Photochem. Photobiol. 34:63 (1981) |
| 5-aminomethyl-8-methoxy-psoralene | Hansen et al., Tet. Lett. 22; 1847 (1981) |
| 4,5,8-trimethylpsoralene | Ben-Hur et al., Biochem. Biophys. Acta 331:181 (1973) |
| 4'-aminomethyl-4,5,8-trimethylpsoralene | Issacs et al., Biochem. 16:1058 (1977) |
| xanthotoxin | Hradecma et al., Acta Virol. (Engl. Ed.) 26:305 (1982) |
| Khellin | Beaumont et al., Biochem. Biophys. Acta 608:1829 (1980) |

Furocoumarins and phenanthridines are preferred as the photochemically reactive unit A.

Particularly preferred photochemically reactive units A are angelicins corresponding to general formula (V)

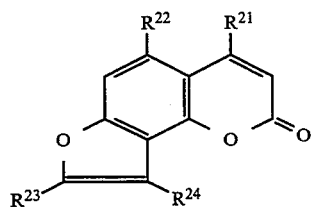

in which
$R^{21}$, $R^{22}$ and $R^{23}$ independently of one another represent hydrogen or $C_{1-4}$ alkyl and
$R^{24}$ is hydrogen, $C_{1-4}$ alkyl, $C_{1-4}$ alkyl substituted by hydroxy, $C_{1-4}$ alkoxy, amino, halogen and/or by the group

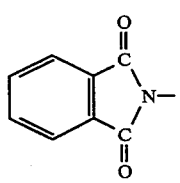

and psoralenes corresponding to general formula (VI)

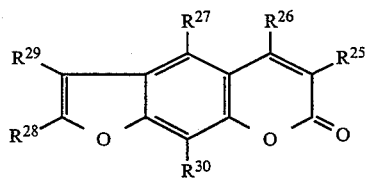

in which
$R^{25}$, $R^{26}$, $R^{27}$ and $R^{28}$ independently of one another represent hydrogen or $C_{1-4}$ alkyl,
$R^{29}$ represents hydrogen, $C_{1-4}$ alkyl, $C_{1-4}$ alkyl substituted by hydroxy, $C_{1-4}$ alkoxy, amino, halogen and/or by

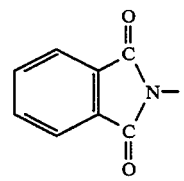

and
$R^{30}$ is hydrogen, hydroxy, $C_{1-4}$ alkyl, carboxy, $C_{1-4}$ alkoxycarbonyl or $C_{1-4}$ alkoxy.

In formulae (V) and (VI), $R^{21}$, $R^{22}$, $R^{23}$ and $R^{25}$, $R^{26}$, $R^{27}$ and $R^{28}$ independently of one another are preferably hydrogen or methyl.

In formula (V), $R^{24}$ is preferably hydrogen, methyl or aminomethyl.

In formula (VI), $R^{29}$ is preferably hydrogen, methyl, hydroxymethyl or aminomethyl and $R^{30}$ is hydrogen, methyl, hydroxy, carboxy or methoxycarbonyl.

4'-Aminomethyl-4,5'-dimethyl angelicins corresponding to formula (Va)

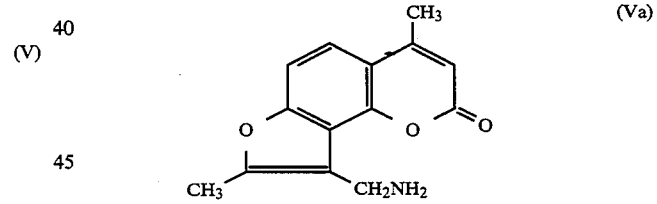

and the compound corresponding to formula (VIa)

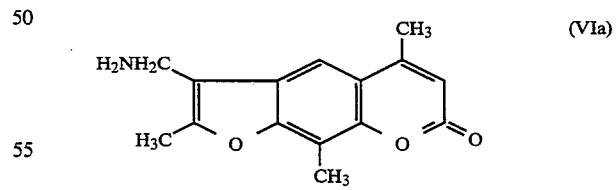

are particularly preferred.

The following angelicins of formula (V) are mentioned by way of example:

| $R^1$ | $R^2$ | $R^3$ | $R^4$ |
|---|---|---|---|
| H | H | H | H |
| $CH_3$ | H | $CH_3$ | H |
| $CH_3$ | $CH_3$ | $CH_3$ | $CH_2OH$ |
| $CH_3$ | H | $CH_3$ | $CH_2OCH_3$ |
| $CH_3$ | H | $CH_3$ | $CH_2NH_2$ |
| $CH_3$ | H | $CH_3$ | $CH_2Cl$ |

| $R^1$ | $R^2$ | $R^3$ | $R^4$ |
|---|---|---|---|
| CH₃ | H | CH₃ | 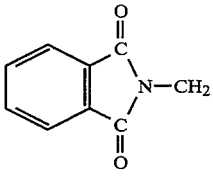 |

The following polymers of formula (I) according to the invention are mentioned by way of example (by angelicin A is meant 4'-aminomethyl-4,5'-dimethyl angelicin):
angelicin A-[polystyrene beads]-angelicin A
angelicin A-(polymer 1)
angelicin A-(polymer 2)-angelicin A
angelicin A-(polymer 3)-angelicin A
monomer unit of polymer 1 containing the chelating group:

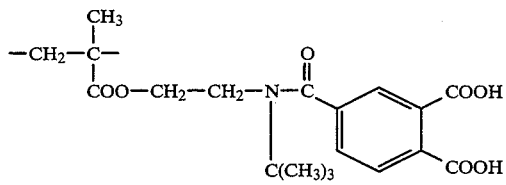

monomer unit of polymer 2:

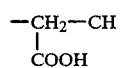

monomer unit of polymer 3 containing the chelating group:

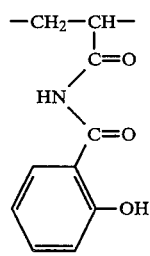

Polystyrene beads are microscopically small (i.e. approx. 10–1000μ), macroporous polystyrene microspheres.

In addition, photochemically linkable polymers according to the invention may contain from their production radical chain initiator units which correspond to the units B-L in formula (I).

The units A and P of the polymers according to the invention are linked to one another, for example, by an ester, sulfonic acid ester, amide, sulfonamide, urethane, thiourethane, urea, thiourea, ether, amine and sulfide group. If increased mobility is required for the units A and/or P, units such as, for example, $C_{1-20}$ alkylene, preferably $C_{3-15}$ alkylene and, more preferably, $C_{5-10}$ alkylene, $C_{6-10}$ arylene-$C_{2-10}$ alkylene, preferably phenylene- or naphthylene-$C_{2-8}$ alkylene, or $(CH_2—CH_2—O)_l$ with $l=1$–20, preferably 3–15 and, more preferably, 5–10, may be incorporated between the linking groups.

The units A and P are preferably linked by an amide, urea, ester or urethane group and, more preferably, by amide and urea groups.

The monomer units are generally known. The polymeric component P may be prepared by generally known polymerization methods.

For example, vinyl monomers are (co)polymerized with radical chain initiators containing the photochemically reactive unit A under standard polymerization conditions, i.e. at temperatures of 30° to 150° C., if desired—or in the case of solid reactants—in (inert) solvents, such as for example dimethyl acetamide, dimethyl formamide, dimethyl sulfoxide, (chlorinated) aromatic hydrocarbons, (chlorinated) aliphatic hydrocarbons, ethers, esters, ketones, alcohols, under atmospheric pressure or—in the case of gaseous monomers—even under excess pressure in an autoclave. If desired, typical additives (such as $\overline{M}_w$ regulators, for example dodecanethiol or n-butylthiol, crosslinking agents in the production of beads, for example divinyl benzene, etc.) may be added to the reaction solution.

The radical chain initiators containing the photochemically reactive unit A (compounds corresponding to formula VII below) may be obtained, for example, by reaction of aminofunctional or hydroxy functional compounds containing the photochemically reactive unit A with radical chain initiators containing (sulfonic) acid chloride or isocyanate groups.

The photochemically reactive unit A present in the polymers corresponding to formula (I) is obtained by means of new photochemically reactive initiators corresponding to general formula (VII)

$$A—L—B(-L—A)_y \qquad (VII)$$

in which
A is the photochemically reactive unit defined above,
B is a radical-forming unit,
L is a linker group and
y is the number 0 or 1.

Suitable linker groups L are sulfonic acid ester, ester, sulfonamide, amide, urethane, thiourethane, urea, thiourea, ether, amine, sulfide.

Preferred linker groups are amides and ureas and/or esters and urethanes. Amides and ureas are particularly preferred.

The linker group L establishes a covalent bond between the photochemically reactive unit and the radical-forming unit B.

In cases where increased mobility is required for units A and/or B, L may also perform a spacer function, in which case L may consist of the following sub-units corresponding to formula (VIII):

$$L^1\text{-}R\text{-}L^1 \qquad (VIII)$$

in which
$L^1$ has the meanings defined for L and
R is $C_{1-20}$ alkylene, preferably $C_{3-15}$ alkylene and, more preferably, $C_{5-10}$ alkylene, $C_{6-10}$ arylene-$C_{2-8}$ alkylene, preferably phenylene- or naphthylene-$C_{2-8}$ alkylene, or $(CH_2—CH_2—O)_n$ where $n=1$ to 20, preferably 3 to 15 and, more preferably, 5 to 10.

The radical-forming unit B may be formed, for example, by the following compounds:

1) Azo structures corresponding to general formula (IX)

$$R^{11}-N=N-R^{12} \quad (IX)$$

in which
R$^{11}$ and R$^{12}$ represent C$_{1-20}$ alkyl, C$_{3-10}$ cycloalkyl, C$_{7-20}$ aralkyl or the group

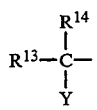

and
Y is CN, N$_3$ or

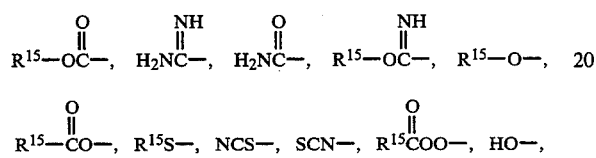

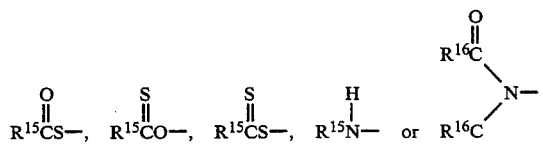

R$^{13}$, R$^{14}$ and R$^{15}$ independently of one another represent C$_{1-20}$ alkyl, C$_{3-6}$ cycloalkyl or, where R$^{13}$ and R$^{14}$ are attached, represent C$_{2-30}$ alkylene or, in addition, one of the substituents R$^{13}$ or R$^{14}$ but not both, represents phenyl, tolyl, xylyl, benzyl or phenethyl, R$^{16}$ independently represents C$_{1-6}$ alkyl, C$_{3-6}$ cycloalkyl or C$_{6-12}$ aryl;

2) Tetraaryl/alkyl ethanes corresponding to general formula (X)

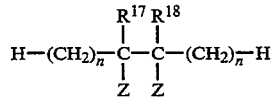

in which
Z represents hydroxy, C$_{1-6}$ alkyl or C$_{6-20}$ aryl, more particularly hydroxy, methyl, ethyl, n- or isopropyl, phenyl or naphthyl, R$^{17}$ and R$^{18}$ independently of one another represent C$_{1-6}$ alkyl or C$_{6-20}$ aryl, more particularly methyl, ethyl, n- or isopropyl, phenyl or naphthyl and n is a number of 1 to 6 and preferably the number 1, 2, 3, 4 or 5;

3) Dinitriles corresponding to formula (XI)

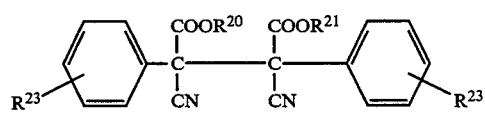

in which
R$^{20}$, R$^{21}$ and R$^{23}$ independently of one another represent (CH$_2$)$_m$H where m is a number of 1 to 6 and preferably the number 1, 2, 3, 4 or 5;

4) Peroxides corresponding to general formula (XII)

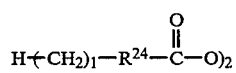

in which
l is a number of 0 to 6, preferably the number 0, 1, 2, 3 or 4 and, more preferably, the number 0, 1 or 2 and R$^{24}$ represents phenylene, naphthylene, C$_{3-6}$ alkylene or C$_{3-6}$ cycloalkylene.

Structures 1) and 4) are preferred for the unit B.

The compounds corresponding to formulae (IX) to (XII) are generally known (cf. for example U.S. Pat. No. 3,956,269, Houben-Weyl, Makromolekulare Stoffe, Part 1, pages 16–19).

Preferred azo structures corresponding to formula (IX) are compounds corresponding to formula (IXa):

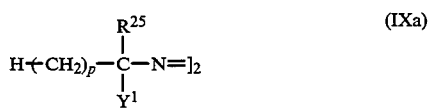

in which
p is a number of 1 to 20, preferably 1 to 15 and, more preferably, 2 to 10, Y$^1$ is CN, N$_3$, COOR$^{26}$ and R$^{25}$ and R$^{26}$ independently of one another represent C$_{1-6}$ alkyl, more particularly methyl, ethyl, n- or isopropyl, or C$_{3-6}$ cycloalkyl, more particularly cyclopropyl, cyclopentyl or cyclohexyl.

A particularly preferred structure for the units B mentioned under 1) has formula (IXb):

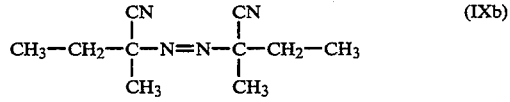

i.e. p is 2, R$^{25}$ is CH$_3$ and Y$^1$ is CN

A particularly preferred structure of the units B mentioned under 4) corresponds to formula (VIII) with l=0 and R$^{24}$=phenylene.

The structures corresponding to formulae (IX) to (XII), which make up the radical-forming unit, bear 1 (y in formula (I)=0) or 2 (y in formula (I)=2) reactive groups X$^1$ (cf. definition of formula (XIII)).

In the azo structures corresponding to formula (IX), the substituents R$^{11}$ and R$^{12}$ bear this/these group(s). In the structures corresponding to formulae (IXa), (IXb), (X) and (XII), the terminal hydrogen atoms are replaced by this/these group(s). The dinitriles corresponding to formula (XI) bear this/these group(s) symmetrically around the central bond in R$^{20}$, R$^{21}$ and/or R$^{23}$.

The following photochemically active initiators corresponding to formula (VII) are listed by way of example (by angelicin A is meant 4'-aminomethyl-4,5'-dimethyl angelicin):

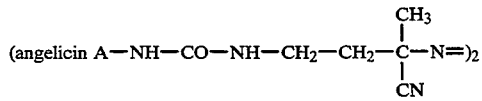

-continued

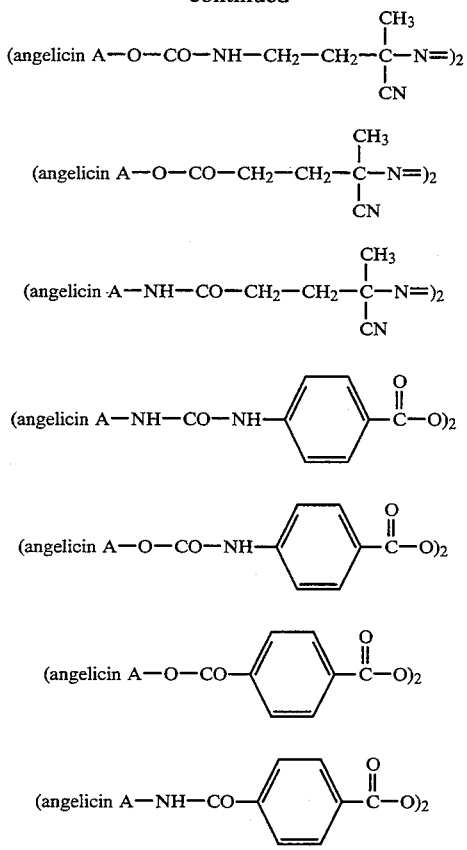

For the production of photochemically active radical chain initiators corresponding to formula (VII)

$$A-L-B(-L-A)_y \qquad (VII)$$

radical-forming compounds corresponding to general formula (XIII)

in which
B is as defined above and
$X^1$ may be NCO, NCS, COCl, COOH, CO—O—NHS, OH, $NH_2$, SH, Cl, Br or I and
y=0 or 1, preferably 0, are reacted with 1 or 2 equivalents of photochemically active substances A in solvents chemically inert to the groups mentioned under $X^1$, such as for example chlorinated aliphatic hydrocarbons, ketones, nitriles, sulfoxides, sulfones, etc., at temperatures in the range from 0° to 40° C.

In the case of compounds corresponding to formula (XIII)

in which
$X^1$ is COCl or $CONHSO_2Cl$, a proton catcher, such as pyridine or triethylene amine for example, is best added to the reaction mixture whereas, where X=COOH, the reaction is carried out in the presence of carbodiimides, for example dicyclohexyl carbodiimide.

Compounds in which $X^1$=NCO or COCl are preferably used as the compound $X^1$—B—$(X^1)_y$ in the process according to the invention.

The reaction is preferably carried out at temperatures of 0° to 30° C., more preferably at temperatures of 15° to 25° C. and, most preferably, at temperatures around 20° C. $CH_2Cl_2$, acetone or acetonitrile is preferably used as the solvent.

The compounds corresponding to general formula (XIII) are generally known or may be produced by generally known methods (cf. for example U.S. Pat. No. 4,155,937).

The linker group L is formed by the reaction of $X^1$ from the formula $X^1$—B—$X^1_y$ with the reactive group in the photochemically reactive unit A, for example the amino group in angelicin A.

The photochemically active radical chain initiators are isolated by methods known per se, for example after filtration of any (ionic) secondary products formed, by evaporation of the solvent in a high vacuum where low-boiling solvents are used or by precipitation by addition of a suitable precipitant, in which case the product according to the invention is generally obtained in pure form. In cases where the secondary products are not volatile or cannot be separated from the compounds according to the invention by dissolution and crystallization or filtration, the compounds according to the invention are isolated by liquid chromatography methods known per se, for example column chromatography or preparative HPLC.

The (thermally) initiated decomposition of the radical chain initiator results in the formation of free radicals which contain the photochemically reactive unit A and which react with the ethylenically unsaturated compounds to form new free radicals which add further ethylenically unsaturated monomers, the growth reaction being terminated by combination of two growing radicals, by disproportionation thereof, hydrogen abstraction or chain transfer (for example where regulators are used). Where the growth reaction is terminated by the first of these reactions, polymers of the formula A-P-A according to the invention are formed whereas, where the growth reaction is terminated by the latter reactions, polymers of the formula A-P according to the invention are formed. In cases where several termination reactions take place at the same time, mixtures of polymers of both formulae according to the invention are formed. The molecular weights of the polymers according to the invention can be adjusted by variations known per se to the experimental details, such as initiator, monomer and, optionally, regulator concentration, temperature and solvent.

By using a mercaptofunctional photochemically reactive unit A-SH, the radical chain polymerization can also be initiated by conventional nonfunctional radical chain initiators, such as for example azoisobutyronitrile or dibenzoyl peroxide, in which case the mercaptofunctional unit A acts both as a chain transfer agent and as a molecular weight regulator.

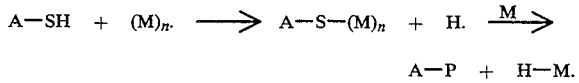

Other processes for the production of polymers A-P according to the invention are characterized in that monomers M suitable for anionic polymerization are reacted under anionic polymerization conditions known per se in the presence of anionic initiators containing the photochemically reactive unit A and, after the desired molecular weight has been reached, the reaction is terminated by addition of the usual proton-active reagents, such as methanol for example. The anionic initiators may be obtained, for example, by reduction (optionally in situ) of the photochemically reactive unit A with sodium or lithium metal in solvents, such as tetrahydrofuran:

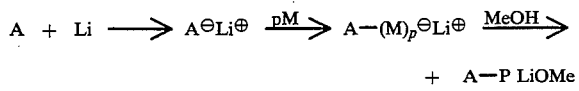

+ A—P LiOMe

Alternatively, other monofunctional and bifunctional initiators (AnI) known per se may be used for the anionic polymerization, in which case the growth reaction may be terminated with functionalizable reagents, such as I$_2$ or BrCN for example, after the desired molecular weight has been reached, followed by linking to hydroxyfunctional or aminofunctional compounds containing the photochemically reactive unit A by a polymer-analogous reaction:

AnI-(M)$_p$$^\ominus$ + Br—CN → AnI-(M)$_p$-Br-CN$^\ominus$

AnI (M)$_p$-Br + A-NH$_2$ → P-A

Another suitable process for the production of dyes according to the invention is the (living) cationic polymerization of appropriate monomers under conditions known per se, i.e. in the presence of cationic initiators (CatI), the growth reaction being terminated after the desired molecular weight has been reached by aminofunctional, thiofunctional or hydroxyfunctional compounds containing the photochemically reactive unit:

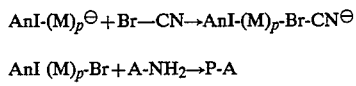

As a modification of living cationic polymerization, the Inifer method is suitable for the preparation of polymers according to the invention (cf. Kennedy, J. P.: Polymer J. 12, 609, (1980), where the functions of initiator and chain transfer agent are performed by one and the same compound.

The functional terminal groups may then be reacted with an aminofunctional or thiofunctional compound containing the photochemically reactive unit A in a polymer-analog reaction.

Another suitable process for the production of polymers A-P-A according to the invention is based on polycondensation reactions in which monomers capable of polycondensation, such as for example diols or diamines and bis-isocyanates or bis-acid chlorides, are subjected in known manner to a condensation reaction which is terminated by compounds containing the photochemically reactive unit A after the desired molecular weight has been reached.

Where they contain functional groups, the polymers according to the invention obtained by these processes may be further reacted by polymer-analog reactions known per se in order in this way to obtain the required property spectrum, for example solubility in water.

It is better and simpler to establish the desired properties through the polymerization of suitable monomers. By virtue of their variety of chemical properties, radical-polymerizable monomers are superior in this regard to the other monomers. Accordingly, the process of free radical chain polymerization using radical chain initiators or chain transfer agents containing the photochemically reactive unit A are preferred.

The photochemically linkable polymers of formula (I) according to the invention may be used for immunological purposes, for example for gene probe tests, or for immobilizing and marking biological substances, such as DNA for example.

The following Examples are intended to illustrate the invention without limiting its scope in any way.

Examples

A) Preparation of photochemically linkable polymers corresponding to formula (I):

Example 1

Angelicin A-[polystyrene beads]-angelicin A

Radical suspension polymerization of styrene beads with the initiator of Example 5

A mixture of 80 ml deionized water, 9 g of a 10% aqueous Mowiol 40-88 ® solution (Hoechst AG) and 0.09 g sodium hydroxide is introduced into a three-necked flask equipped with a high-speed paddle stirrer, thermometer and dropping funnel. The reaction flask is purged with nitrogen and its contents are heated to 75° C. and stirred at 750 r.p.m.

A mixture of 30 g styrene, 1.9 g divinylbenzene, 5.6 g cyclohexane and 3 g of the radical initiator of Example 5 is added over a period of 30 minutes, followed by stirring for another 2 h. 5 ml deionized water and 4.5 g of a 10% aqueous Mowiol 40-88 ® solution are then added and the mixture is stirred for another 6 h.

The cyclohexane is distilled off from the reaction mixture in a water jet vacuum. After cooling, the reaction mixture is made up with 500 ml deionized water and, after the beads have sedimented, is poured through a 40 μm mesh sieve. The product thus isolated is washed with methanol and dried.

The polystyrene beads have a particle size of 200 to 300 μm.

Example 2

Angelicin A-(polymer 2)-angelicin A

Radical polymerization of acrylic acid with the initiator of Example 5

5 g acrylic acid are dissolved under nitrogen in 10 ml dimethyl sulfoxide and 10 ml deionized water, heated to 65° C. and 50 mg of the radical initiator of Example 5 are added. After stirring for 2 h, the highly viscous solution is diluted with 20 ml deionized water and then stirred for another 15 h. The crude polymer is precipitated in acetone, filtered off under suction and dried in a high vacuum. It has a limiting viscosity of 8.5 dl/g, as measured on a 0.9% NaCl solution at 20° C.

Example 3

Angelicin A-(polymer 1)-angelicin A

Radical polymerization of $$\begin{array}{c} CH_3 \\ | \\ CH_2=C \\ | \\ COO-CH_2-CH_2-N-C \\ \phantom{COO-CH_2-CH_2-N}| \phantom{-C} \\ \phantom{COO-CH_2-CH_2-N}C(CH_3)_3 \end{array} \underset{\phantom{xxxx}COOH}{\overset{\phantom{xxxx}COOH}{\underset{\phantom{xxx}}{\bigcirc}}}$$

with the initiator of Example 5

5 g of the above-mentioned monomer are polymerized with 50 mg of the radical initiator of Example 5 with addition of 1.075 g sodium hydroxide under the conditions described in Example 2. The polymer has a limiting viscosity of 2.4 dl/g, as measured on a 0.9% NaCl solution at 20° C.

Example 4

Angelicin A-(polymer 3)-angelicin A

Polymer 3:

$$-CH_2-CH- \\ \phantom{-CH_2-}| \\ \phantom{-CH_2-}CO-NH-CO-\bigcirc\!\!\!-OH$$

3 g of the powdered polymer of Example 2 (angelicin A-(polymer 2)-angelicin A) are suspended under nitrogen in a solution of 28.5 g (salicylic acid amide in xylene (50 ml)) and distilled thionyl chloride (24.8 g) is added dropwise. The mixture is allowed to react for 12 h at 90° C. The resulting powder is filtered off, washed three times with xylene and dried in a high vacuum.

The product shows two strong IR absorption bands 1700 cm$^{-1}$ and 1660 cm$^{-1}$ characteristic of C=O and a band of medium strength at 3250 cm$^{-1}$ characteristic of N—H B) Preparation of photochemically active radical chain initiators corresponding to formula (VII)

Example 5

1 mmol 4'-aminomethyl-4,5'-dimethyl angelicin and 1 mmol 3,3'-dicyano-3,3'-azodibutyl isocyanate are stirred in 20 ml anhydrous CH$_2$Cl$_2$ at room temperature in an atmosphere of high-purity nitrogen until the IR band of the NCO group has disappeared, after which the solvent is removed by evaporation in a rotary evaporator at room temperature. The residue gives the product according to the invention in pure form ($^1$H-NMR).

Urea protons: 5.4 and 5.82 ppm (triplets)
Aromatic protons 7.25 ppm (doublet),
of angelicin: 7.32 ppm (doublet) 6.07 ppm (singlet)

Example 6 p,p'-bis-isocyanatomethyl benzoyl peroxide is reacted with 4'-aminomethyl-4,5'-dimethyl angelicin in CH$_2$Cl$_2$ as described in Example 5. The reaction product is isolated and characterized by IR spectroscopy (>C=O urea 1685 cm$^{-1}$).

Example 7

1 mmol 4,4'-dicyano-4,4'-azodipentanoyl chloride and 1 mmol 4'-hydroxymethyl-4,5'-dimethyl angelicin are stirred in 20 ml anhydrous CH$_2$Cl$_2$ and 1.1 mmol pyridine in an atmosphere of high-purity nitrogen until the IR band of the COCl group has disappeared. On completion of the reaction, pyridinium hydroxide chloride is filtered off and the filtrate is concentrated by evaporation in vacuo in a rotary evaporator at room temperature. The product obtained is pure ($^1$H-NMR).

$^1$H-NMR:

| | | |
|---|---|---|
| Angelicin allyl ester protons: | 4.4 ppm | |
| Angelicin aromatic protons: | 6.12 ppm | singlet |
| | 7.3 ppm | doublets |
| | 7.37 ppm | |

C) Use of the polymers of formula (I) (marking of DNA)

Example 8

Photoreaction of angelicin A-(polymer 2)-angelicin A (cf. Example 2) with DNA

5 μl (0.4 μg DNA/μl) of a 1.7 kb DNA fragment are exposed to light for 1 hour at 365 nm with 2 μl of a solution of the photoreactive polyacrylic acid of Example 2 in dimethyl formamide (10.6 mg/ml). To observe the binding behavior, the reaction mixture is separated up by agarose gel electrophoresis (0.5% to 1% agarose, 1X TBE buffer (TBE=TRIS[tris(hydroxymethoxyl)-methylamine]-borate EDTA); 60 V; 2 H). The reaction mixtures in which a photoreaction was carried out with DNA show distinctly "lagging" (reduced migration) of the DNA laden with the photochemically modified polymer compared with unexposed batches of pure 1.7 kb DNA.

Example 9

Photoreaction of angelicin A-(polymer 1)-angelicin A (cf. Example 3) with DNA

2 μl of a solution of the polymer of Example 3 in 0.1M sodium borate buffer, pH 8.5, in a concentration of 2 mg/ml were reacted in the same way with 5 μl DNA solution (1.7 kb; 0.4 μg/ul). Subsequent electrophoresis also revealed a shift in the mobility of the marked DNA whereas the control experiments with unexposed batches and initiator showed only negligible changes in the running behavior.

We claim:

1. A photochemically linkable polymer corresponding to formula (I)

$$\text{P-(A)}_n \hspace{2cm} (I)$$

in which

P is a polymer component, which is linear, branched or crosslinked, the monomer units for the polymer component being selected from the group consisting of acrylic, methacrylic, vinyl, styryl units, and mixtures thereof, and wherein the monomer units may contain reactive or activatable groups which allow covalent attachment of chelating agents, or wherein P is a polyurethane or polyurea, and in the event that P comprises an uncrosslinked, nonionic polymer component, then P has an average molecular weight ($\overline{M}_w$) of from 1,000 to 10,000,000, the polymer component optionally further comprising chelating agents attached to the polymer component at the reactive or activatable groups;

A is selected a photochemically reactive moiety selected from the group consisting of acridines, furocoumarins, phenanthridines, phenazines, phenothiazines, quinolines, anthracyclines, netropsin, distamycin and bisbenzimidazoles; and n is the number 1 or 2.

2. A photochemically linkable polymer according to claim 1, in which

P is a polymer component wherein the monomer units are based on:

i) compounds corresponding to formula (II)

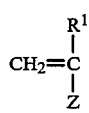
(II)

in which

Z is hydrogen, $C_1$-$C_{20}$ alkyl, —CO—OR$^2$, —CO—NR$^3$—R$^4$ or —OOCR$^5$ and R$^1$, R$^2$, R$^3$, R$^4$ and R$^5$ independently of one another represent hydrogen or $C_1$-$C_{20}$ alkyl; or ii) one or more of styrene, α-methyl styrene, or compounds corresponding to formula (III)

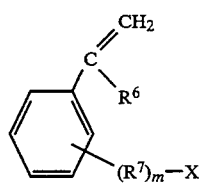
(III)

wherein

R$^6$ is hydrogen or methyl,

R$^7$ is CH$_2$ or SO$_2$, m is 0 or 1, and

X is halogen, SO$_2$—CH$_2$—CH$_2$ halogen, OMe, SO—CH$_3$ or methyl, wherein Me is an equivalent of a metal; or iii) one or more of 1- and 2-vinyl naphthalene, 1-vinyl carbazole, or compounds corresponding to formula (IV)

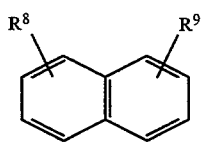
(IV)

in which

R$^8$ is hydrogen, SO$_3$H, COOH, SO$_3$Me or COOMe, where Me is an equivalent of a metal and R$^9$ represents

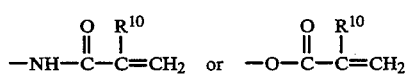

where R$^{10}$ is hydrogen or methyl, and wherein the polymer component P further comprises chelating agents, the chelating agents being obtained from one or more of compounds (C$_1$) to (C$_4$):

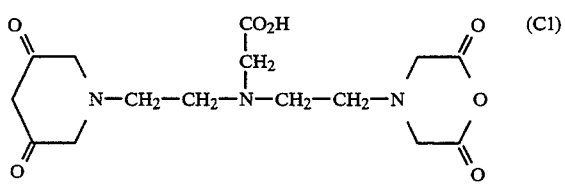
(C1)

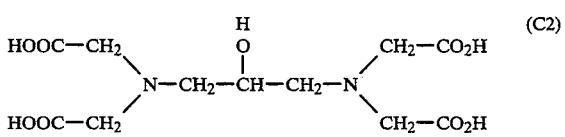
(C2)

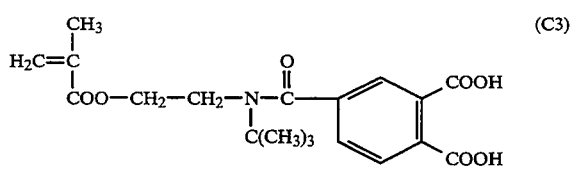
(C3)

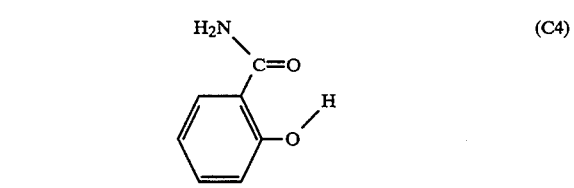
(C4)

and wherein

A stands for either:

an angelicin corresponding to general formula (V)

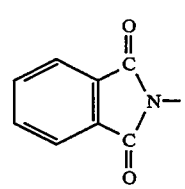
(V)

in which

R$^{21}$, R$^{22}$ and R$^{23}$ independently of one another represent hydrogen or $C_1$-$C_4$ alkyl and R$^{24}$ is hydrogen, $C_1$-$C_4$ alkyl, $C_1$-$C_4$ alkyl substituted by hydroxy, $C_1$-$C_4$ alkoxy, amino, halogen and/or by the group or a psoralene corresponding to the general formula (VI)

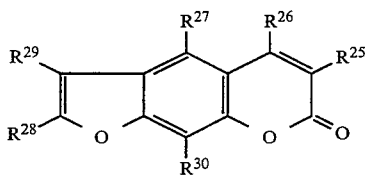
(VI)

in which
R$^{25}$, R$^{26}$, R$^{27}$ and R$^{28}$ independently or one another represent hydrogen or C$_1$-C$_4$ alkyl,
R$^{29}$ represents hydrogen, C$_1$-C$_4$ alkyl, C$_1$-C$_4$ alkyl substituted by hydroxy, C$_1$-C$_4$ alkoxy, amino, halogen and/or by

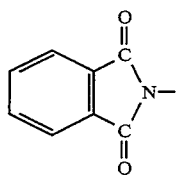

and
R$^{30}$ is hydrogen, hydroxy, C$_1$-C$_4$ alkyl, carboxy, C$_1$-C$_4$ alkoxycarbonyl or C$_1$-C$_4$ alkoxy.

3. A photochemically linkable polymer according to claim 1, wherein
P is a polymer component wherein the monomer unit is one or more of the following:

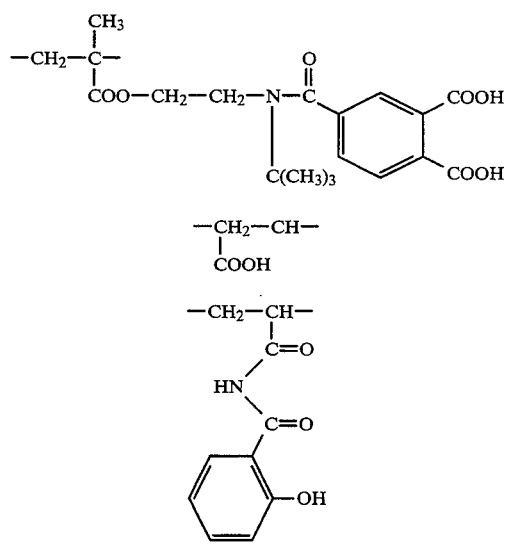

and wherein
A stands for:
an angelicin corresponding to general formula (V)

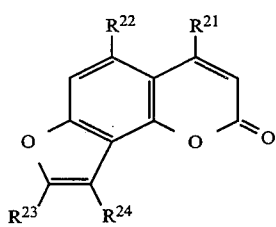
(V)

in which
R$^{21}$, R$^{22}$ and R$^{23}$ independently of one another represent hydrogen or C$_1$-C$_4$ alkyl and R$^{24}$ is hydrogen, C$_1$-C$_4$ alkyl, C$_1$-C$_4$ alkyl substituted by hydroxy, C$_1$-C$_4$ alkoxy, amino, halogen and/or by the group

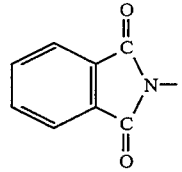

or a psoralene corresponding to the general formula (VI)

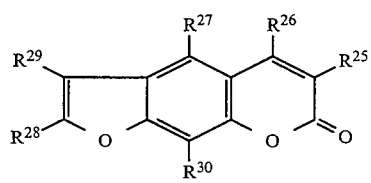
(VI)

in which
R$^{25}$, R$^{26}$, R$^{27}$ and R$^{28}$ independently or one another represent hydrogen or C$_1$-C$_4$ alkyl,
R$^{29}$ represents hydrogen, C$_1$-C$_4$ alkyl, C$_1$-C$_4$ alkyl substituted by hydroxy, C$_1$-C$_4$ alkoxy, amino, halogen and/or by

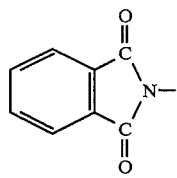

and
R$^{30}$ is hydrogen, hydroxy, C$_1$-C$_4$ alkyl, carboxy, C$_1$-C$_4$ alkoxycarbonyl or C$_1$-C$_4$ alkoxy.

4. A biological molecule labeled with the photochemically linkable polymer of claim 1.

5. The biological molecule of claim 4, consisting of a protein or nucleic acid.

6. A photochemically linkable polymer as claimed in claim 1, wherein the polymer component (P) contains reactive or activatable groups selected from the group consisting of acid halide, imide ester, benztriazolyl, isocyanato, isothiocyanato, oxirane, and diimide groups.

7. A photochemically linkable polymer as claimed in claim 1, wherein the polymer component (P) is a linear molecule.

8. A photochemically linkable polymer as claimed in claim 1, wherein the polymer component (P) is a branched molecule.

9. A photochemically linkable polymer as claimed in claim 1, wherein the polymer component (P) is a crosslinked molecule.

10. A photochemically linkable polymer as claimed in claim 1, wherein the polymer component (P) contains water-solubilizing groups.

11. A photochemically linkable polymer as claimed in claim 1, which is soluble in aqueous buffered solution.

* * * * *